United States Patent [19]

Ogata et al.

[11] Patent Number: 5,241,121
[45] Date of Patent: Aug. 31, 1993

[54] PROCESS FOR PREPARATION OF 4,4'-DIHYDROXYDIPHENYLSULFONE

[75] Inventors: Eiji Ogata, Wakayama; Nobuyuki Nate, Kainan; Kazuo Hamano, Wakayama, all of Japan.

[73] Assignee: Konishi Chemical Ind. Co., Ltd., Wakayama, Japan

[21] Appl. No.: 904,887

[22] Filed: Jun. 25, 1992

Related U.S. Application Data

[63] Continuation of Ser. No. 752,589, filed as PCT/JP90/01740 on Dec. 28, 1990, abandoned.

[30] Foreign Application Priority Data

Dec. 29, 1989 [JP] Japan ................................. 1-340699
Dec. 29, 1989 [JP] Japan ................................. 1-340700

[51] Int. Cl.$^5$ .................. C07C 315/06; C07C 315/00
[52] U.S. Cl. ........................................... 568/33
[58] Field of Search ............................... 568/33

[56] References Cited

U.S. PATENT DOCUMENTS

| | | | |
|---|---|---|---|
| 2,392,137 | 1/1946 | Foster | 508/33 |
| 2,833,838 | 5/1958 | Sauls | 585/536 |
| 3,065,274 | 11/1962 | Vegler et al. | 568/33 |
| 4,162,270 | 7/1979 | Ogata et al. | 568/33 |
| 4,382,147 | 5/1983 | Kitamura et al. | 568/33 |
| 4,820,831 | 4/1989 | Ogata et al. | 568/33 |
| 4,996,367 | 2/1991 | Ernst et al. | 568/33 |

FOREIGN PATENT DOCUMENTS

| | | |
|---|---|---|
| 0293037 | 11/1988 | European Pat. Off. . |
| 2200004 | 4/1990 | European Pat. Off. . |
| 43-24660 | 10/1968 | Japan . |
| 47-43936 | 11/1972 | Japan . |
| 61-24559 | 2/1986 | Japan . |
| 2-235857 | 9/1990 | Japan . |
| 2-282358 | 11/1990 | Japan . |
| 2030566 | 4/1980 | United Kingdom . |

OTHER PUBLICATIONS

Derwent Abs. 01008x/01; Mitsubishi Gas Chem. Prod. Feb. 20, 1974, JA-020327; 4,4'-dihydroxydiphenylsulphone . . . .
J. Chem. Soc. 2854-6 (1949), Hinkel et al.

*Primary Examiner*—Marianne M. Cintins
*Assistant Examiner*—Michael B. Hydorn
*Attorney, Agent, or Firm*—Armstrong, Westerman, Hattori, McLeland & Naughton

[57] ABSTRACT

A process for preparing 4,4'-dihydroxydiphenylsulfone, the process including heating 4,4'-dihydroxydiphenylsulfone and 2,4'-dihydroxydiphenylsulfone in the presence of an acid catalyst to isomerize the 2,4'-dihydroxydiphenylsulfone into 4,4'-dihydroxydiphenylsulfone, the process being characterized in that a suspension of 4,4'-dihydroxydiphenylsulfone and 2,4'-dihydroxydiphenylsulfone in a liquid dispersing medium is heated for isomerization while the liquid portion is distilled off or a crystal mixture of 4,4'-dihydroxydiphenylsulfone and 2,4'-dihydroxydiphenylsulfone is heated for isomerization to produce 4,4'-dihydroxydiphenylsulfone in the form of crystal powder.

7 Claims, No Drawings

PROCESS FOR PREPARATION OF 4,4'-DIHYDROXYDIPHENYLSULFONE

This application is a continuation of application Ser. No. 07/752,589 filed as PCT/JP90/01740 on Dec. 28, 1990, now abandoned.

FIELD OF THE INVENTION

The present invention relates to a process for preparing 4,4'-dihydroxydiphenylsulfone (hereinafter referred to as "4,4'-DDS").

BACKGROUND ART

In recent years, a demand for 4,4'-DDS has increased in the chemical industry, e.g. fields of fibers, resins or the like. Furthermore, there has arisen a need for an extremely high-purity 4,4'-DDS to improve the quality of products in each field.

A process for preparation of 4,4'-DDS is known in which a phenol and a sulfonating agent are subjected to dehydration reaction in the presence of a solvent such as dichlorobenzene which is capable of dissolving the foregoing materials and the produced 4,4'-DDS. However, when the dehydration reaction is conducted in a solvent as in said process, the desired 4,4'-DDS as dissolved in the reaction product has an isomerization equilibrium with an isomer that is, 2,4'-dihydroxydiphenylsulfone (hereinafter referred to as "2,4'-DDS") is produced as a by-product so that the obtained crude product contains 20 to 30% by weight of 2,4'-DDS as the impurity which decreases the purity and the yield of 4,4'-DDS. Further, it has been recently recognized that trihydroxytriphenyldisulfone (hereinafter referred to as "tri-compound") is produced as a by-product along with 2,4'-DDS.

In view of the above problems, the present inventors proposed a process for preparing a high-purity 4,4'-DDS in a high yield in which a phenol and sulfuric acid undergo dehydration reaction in the presence of a solvent, and the 2,4'-DDS produced as a by-product is isomerized into 4,4'-DDS while gradually removing the solvent from the reaction mixture (Japanese Examined Patent Publication No.55-8972). The proposed process is intended to increase the purity and the yield of 4,4'-DDS in the following manner. In the process, only the 4,4'-DDS is precipitated from the reaction system by gradually removing the solvent utilizing the difference between 4,4'-DDS and 2,4'-DDS in the solubility in the solvent, whereby the isomerization equilibrium is shifted in the solution to induce the isomerization of 2,4'-DDS into 4,4'-DDS. However, on removal of the solvent, the process causes the solidification of the reaction product solution into a non-fluidic viscous solid, and thus necessitates a special type of stirrer of high mechanical strength, resulting in difficulty in provision of a large-size manufacturing apparatus for mass production.

Recently proposed is a process in which while a phenol and sulfuric acid are subjected to dehydration reaction with heating in the presence of an aliphatic hydrocarbon suspending agent and an azeotropic agent, the 2,4'-DDS produced in the reaction is isomerized into 4,4'-DDS (Japanese Unexamined Patent Publication No.64-9970). However, the proposed process necessitates isomerization at a high temperature under fully controlled temperature conditions over a prolonged period of time. Furthermore, since the 2,4'-DDS is isomerized into 4,4'-DDS as suspended in a suspending agent, the process requires a large-size manufacturing apparatus and is unavoidably uneconomical from a thermal standpoint.

DISCLOSURE OF THE INVENTION

An object of the present invention is to provide a process for preparing a high-purity 4,4'-DDS in the form of crystal powder, the process comprising conveniently and easily isomerizing 2,4'-DDS in the reaction mixture containing 2,4'-DDS and 4,4'-DDS into 4,4'-DDS.

Another object of the invention is to provide a process in which the isomerization reaction of the produced 2,4'-DDS into 4,4'-DDS can be easily performed using a conventional stirrer.

According to the present invention, there is provided a process for preparing 4,4'-DDS, the process comprising heating 4,4'-DDS and 2,4'-DDS in the presence of an acid catalyst to isomerize the 2,4'-DDS into 4,4'-DDS, the process being characterized in that either a suspension of 4,4'-DDS and 2,4'-DDS in a liquid dispersing medium is heated for isomerization while the liquid portion is distilled off or a crystal mixture of 4,4'-DDS and 2,4'-DDS is heated for isomerization to produce 4,4'-DDS in the form of crystal powder, the suspension being heated while the liquid portion is distilled off to remove the whole liquid portion on or before the completion of the isomerization reaction.

The inventors' research found the following. When a suspension of 4,4'-DDS, 2,4'-DDS and an acid catalyst is heated to isomerize 2,4'-DDS into 4,4'-DDS while gradually distilling off the liquid portion to remove the whole liquid portion on or before the completion of the isomerization reaction (hereinafter referred to as "isomerization of suspension phase"), the reaction for the isomerization of 2,4'-DDS into 4,4'-DDS smoothly proceeds, producing an extremely high purity 4,4'-DDS in the form of crystal powder with high efficiency. Further, when a crystal powder mixture of 4,4'-DDS and 2,4'-DDS is heated in the presence of an acid catalyst to isomerize 2,4'-DDS into 4,4'-DDS (hereinafter referred to as "isomerization of solid phase"), the reaction for the isomerization of 2,4'-DDS into 4,4'-DDS smoothly proceeds, producing an extremely high purity 4,4'-DDS in the form of crystal powder with high efficiency.

According to the invention, the foregoing isomerization reaction of either the suspension or crystal powder mixture can proceed while retaining the state of suspension or the state of crystal powder of no consistency (free flowing) in which the reaction system can be easily stirred by a conventional stirrer. Moreover, the isomerization reaction of the suspension proceeds without the likelihood to involve coagulation or sedimentation of DDS (4,4'-DDS and 2,4'-DDS). The isomerization reaction of the crystal powder mixture proceeds while maintaining the crystal powder free from consistency. The isomerization reaction of the suspension, although concurring with the distillation of the liquid portion, is unlikely to cause the problem of increasing the consistency and eventually gives 4,4'-DDS as crystal powder of no consistency which can be easily handled by a conventional stirrer. Furthermore, the process of the invention allows the isomerization reaction to proceed at a relatively low temperature and to complete in a relatively short time, and is extremely economical in terms of apparatus volume and from a thermal standpoint.

Usable as the suspension of 4,4'-DDS and 2,4'-DDS for the isomerization reaction of the invention is a suspension of 4,4'-DDS and 2,4'-DDS in a liquid dispersing medium. The foregoing liquid dispersing medium is not specifically limited insofar as it can suspend 4,4'-DDS and 2,4'-DDS. Examples of useful liquid dispersing mediums include mesitylene, aliphatic hydrocarbon suspending agents, among which mesitylene is preferred. The ratio of 4,4'-DDS and 2,4'-DDS in said suspension can be selected from a wide range. Usually it is advantageous to use a suspension which contains about 4% or more by weight of 2,4'-DDS based on the total weight of 4,4'-DDS and 2,4'-DDS. The process of the present invention is operative even when a suspension contains 2,4'-DDS in a higher proportion than 4,4'-DDS. The content of acid catalyst to be used can be suitably selected from a wide range upward from a catalytic amount required for accelerating the isomerization reaction. The content of the acid catalyst is suitably about 0.5% by weight or more, usually about 0.5 to about 5.0% by weight, based on the total weight of 4,4'-DDS and 2,4'-DDS. The isomerization reaction rapidly proceeds even in using more than 5.0% by weight of acid catalyst although economically disadvantageously. The suspensions of 4,4'-DDS and 2,4'-DDS which can be advantageously used in the invention include, for example, a suspension obtained by the dehydration reaction of phenol and sulfonating agent in a liquid dispersing medium which is incapable of dissolving 4,4'-DDS. The above suspension contains the phenolsulfonic acid produced as a reaction intermediate during the dehydration reaction or used as a sulfonating agent among the starting materials. Since the phenolsulfonic acid acts as an acid catalyst for the isomerization reaction, the acid is used as it is in the isomerization of suspension phase according to the invention.

The crystal powder mixture of 4,4'-DDS and 2,4'-DDS which is used for the isomerization of solid phase in the invention is a mixture containing 2,4'-DDS and 4,4'-DDS at the desired ratio which is selectable from a wide range. Usually an advantageously usable mixture contains about 4% or more by weight of 2,4'-DDS based on the total weight of 4,4'-DDS and 2,4'-DDS. The desired isomerization of solid phase according to the invention is induced even when a mixture contains 2,4'-DDS in a higher proportion than 4,4'-DDS. The content of the acid catalyst to be used can widely vary over the range upward from a catalytic amount required for accelerating the isomerization reaction. The content of the acid catalyst to be used is suitably about 0.5% or more, usually about 0.5 to about 5.0% by weight, based on the combined amount of 4,4'-DDS and 2,4'-DDS. The isomerization reaction rapidly proceeds even in using more than 5.0% by weight of acid catalyst although economically disadvantageously. Advantageously usable as such mixture is a reaction mixture of 4,4'-DDS and 2,4'-DDS obtained by the dehydration reaction of phenol and sulfonating agent. Stated more specifically, the crystal powder mixture of 4,4'-DDS and 2,4'-DDS containing the phenolsulfonic acid as adsorbed thereon which has been produced as a reaction intermediate or has been used as the starting material is obtained by separating into solids and liquids the reaction mixture obtained as the solution or suspension of the crystal mixture of crystals of 4,4'-DDS and 2,4'-DDS as a by-product in a liquid dispersing medium. The adsorbed phenolsulfonic acid advantageously acts as an acid catalyst for the isomerization reaction. Therefore, according to the isomerization of solid phase in the invention, the crystal powder mixture obtained by the separation into solids and liquids can be subjected, as it is, to isomerization reaction.

The crystal powder mixture of 4,4'-DDS and 2,4'-DDS which is used in the isomerization of solid phase in the invention can be used regardless of the process for preparing the mixture. The crystal powder mixture obtained by the dehydration reaction of phenol and sulfonating agent or phenolsulfonic acid is advantageously used.

The method of the dehydration reaction will be briefly described below.

Sulfonating agents useful for the dehydration reaction are various and include a wide range of those which are capable of introducing sulfonyl group into a phenol, such as concentrated sulfuric acid, sulfuric anhydride, fuming sulfuric acid, chlorosulfonic acid, phenolsulfonic acid, etc. The ratio of the phenol and sulfonating agent is not specifically limited and can be suitably selected from a wide range. However, usually these components are preferably used in stoichiometric amounts or similar ones or in a ratio such that the former is used in excess of the latter.

The foregoing dehydration reaction is conducted in the presence of a liquid dispersing medium (suspending medium) which is capable of suspending the produced crystals. Useful suspending mediums include, for example, the mesitylene disclosed in PCT/JP90/01179 which was filed on the invention previously made by the present inventors, and the straight-chain or branched-chain aliphatic hydrocarbon and aliphatic halogenated hydrocarbon disclosed in Japanese Unexamined Patent Publication No.64-9970. When an aliphatic hydrocarbon suspending medium is used, the water produced as a by-product needs to be removed from the reaction system using an azeotropic agent according to the disclosure of said unexamined patent publication. Among these suspending mediums, mesitylene is most preferably used. The amount of the liquid dispersing medium to be used is not specifically limited and can vary over a wide range upward from the amount sufficient to stir the reaction system and to effect reflux. In view of economy, the amount of mesitylene is usually up to about 5 times the amount of phenol. Yet mesitylene can be used in excess of said level.

The dehydration reaction can be conducted in a conventional manner. Usually the dehydration reaction is performed by separating and removing the produced water while refluxing the liquid dispersing medium with stirring. Usually the reaction temperature is suitably selected from the range of 120° to 220° C. When the dehydration reaction proceeds while the produced 4,4'-DDS and 2,4'-DDS (which in combination will be hereinafter referred to as "DDS") are suspended in mesitylene, the reaction is performed with stirring more preferably by subjecting the water produced as a by-product to azeotropic distillation with mesitylene at a relatively low temperature of 140° to 165° C. for the separation and removal of the water, while refluxing the mesitylene. When the dehydration reaction is conducted in mesitylene, the reaction system can be more easily stirred and the produced DDS is more stably suspended as fine particles than when the reaction is made in other suspending mediums or solvents to be described later. Furthermore, mesitylene is advantageously used since its use eliminates the need for special attention to the rate of elevating the temperature of the reaction system and facilitates the control of the temperature. Moreover, the obtained suspension contains 4,4'-DDS in a high purity and thus is suitably used in the process of the invention.

The thus obtained suspension of 4,4'-DDS and 2,4'-DDS usually contains about 4 to about 15% by weight of 2,4'-DDS and about 1 to about 5% by weight of phenolsulfonic acid, based on the total weight of 4,4'-DDS and 2,4'-DDS, and is advantageously used, as it is, for the isomerization of suspension phase in the invention. When the isomerization of solid phase is conducted, a crystal powder mixture free from consistency (free flowing) obtained by separation of suspension into solids and liquids may be used. In using such crystal powder mixture, the phenolsulfonic acid is present as adsorbed on the particulate crystal. Furthermore, when mesitylene is used as the suspending agent, the obtained DDS is a powder free from consistency (free flowing) having a light pink color and containing 4,4'-DDS in a high purity. Therefore, the powder is suitably used in the isomerization of solid phase in the invention.

The DDS obtained by dehydration reaction of phenol and sulfonating agent in a solvent which is capable of dissolving the produced 4,4'-DDS can be also used for the isomerization reaction of the invention. When the dehydration reaction is conducted in a solvent, a solid phase containing the produced DDS is separated from the reaction mixture in a conventional manner and pulverized by crushing when so required to provide a powder which can be used for the isomerization of solid phase in the invention. A suspension prepared by suspending the obtained solid phase in a liquid dispersing medium can be used for the isomerization of suspension phase. The solid phase contains about 10 to about 30% by weight of 2,4'-DDS based on the total weight of 4,4'-DDS and 2,4'-DDS, and about 3 to about 10% by weight, based on the weight of DDS, of phenolsulfonic acid adsorbed on DDS which acid has been produced as a reaction intermediate during the dehydration reaction or used as the starting material. Examples of useful solvents are chlorobenzene, dichlorobenzene, trichlorobenzene, chlorotoluene, diethylbenzene, decalin, tetralin, tetrachloroethane, etc. Processes for preparing 4,4'-DDS using such solvents are disclosed, for example, in Japanese Examined Patent Publications Nos. 38-5274, 43-24660, 47-43936 and 55-8972 and Japanese Unexamined Patent Publication No. 61-243060.

The method for separating the DDS crystal powder mixture from the reaction mixture obtained by the above dehydration reaction in the suspending medium or solvent is not specifically limited and can be any of various known methods. Conventional methods employable in this invention include a filtration method, a decantation method, a distillation method, an instantaneously drying method and the like. When the reaction mixture obtained by the dehydration reaction in a solvent contains a small quantity of crystals, the filtration or decantation method is conducted by separating the solid phase from the reaction mixture after increasing the amount of crystals as by cooling or partially distilling off the liquid portion. When the solid phase is obtained in the form of a mass, it is crushed into particles. The liquid components are separated and removed until the crystal powder is made free from consistency (free flowing).

In isomerization of a suspension containing 4,4'-DDS and 2,4'-DDS in the invention, the suspension is heated in the presence of an acid catalyst to make the progress of reaction for isomerization of 2,4'-DDS into 4,4'-DDS while distilling off the liquid portion. When the suspension is free of an acid catalyst, or when more acid catalyst is needed than is present in the suspension obtained by the dehydration reaction, an acid catalyst may be added. Useful acid catalysts include not only phenolsulfonic acid, but also benzenesulfonic acid, benzenedisulfonic acid, chlorobenzenesulfonic acid and the like.

It is essential in the present invention to perform the isomerization of suspension phase while the liquid portion is gradually distilled off. The isomerization may be effected with stirring while evaporating and collecting the liquid portion under a controlled reduced pressure or under normal pressure. The heating temperature may be suitably selected depending on the reduction of pressure, the boiling point of liquid portion, the time taken for the collection, etc. A suitable heating temperature is usually about 120° to about 200° C., and preferably 140° to 180° C. The isomerization reaction is usually completed in about 0.5 to about 10 hours. The distillation of the liquid portion may be completed substantially simultaneously with or prior to the completion of isomerization. In either case, the reaction system is unlikely to become viscous during the distillation of liquid portion, and DDS is suspended as crystals in the suspending medium but is made into a crystal powder mixture of no consistency (free flowing) by the distillation of liquid portion. Therefore, even when isomerization reaction is continued after distilling off the liquid portion before the completion of isomerization, the isomerization of solid phase can be easily conducted while mixing the crystal powder of no consistency (free flowing).

In the isomerization of solid phase in the invention, 2,4'-DDS is isomerized into 4,4'-DDS by heating a DDS crystal powder mixture in the presence of an acid catalyst. The DDS crystals obtained by the aforesaid dehydration reaction usually contains the phenolsulfonic acid as adsorbed thereon which has been produced as a reaction intermediate in the dehydration reaction or has been used as the starting material. The phenolsulfonic acid which acts as an acid catalyst for the isomerization reaction can be advantageously used, as it is, for the isomerization of solid phase in the invention. However, the method for isomerization of solid phase according to the invention is operative using not only such DDS but also the crystal powder mixture of 4,4'-DDS and 2,4'-DDS obtained by any other method. In such event, when the DDS crystal powder mixture does not contain an acid catalyst adsorbed thereon or when more acid catalyst is needed than is present in the crystal powder mixture obtained by the dehydration reaction, an acid catalyst may be added to and adsorbed on the particles in the crystal powder mixture of DDS or at least 2,4'-DDS. The acid catalysts of the type to be used in the isomerization of suspension phase can be used in this case.

The isomerization of solid phase in the invention is conducted in a closed or open container by heating preferably at about 120° to about 200° C., more preferably at about 140° to 180°, at normal or reduced pressure with stirring when so required. The isomerization reaction involving stirring can be easily performed using a conventional powder-handling apparatus, such as a vacuum dryer or the like. The isomerization reaction in the invention which may be carried out in the air is preferably conducted in the atmosphere of nitrogen or like inert gas to prevent oxidation of the obtained product in air.

Thus according to the present invention, a high-purity 4,4'-DDS can be produced in the form of crystal powder of no consistency (free flowing) free of liquid component without need for a procedure for the separation and removal of the solvent or suspending medium after isomerization. When required, the obtained crystal powder is purged into caustic soda to obtain an aqueous solution of the reaction product dissolved as a sodium salt. When required, the aqueous solution is salted out after filtration with activated charcoal to achieve decolorization, whereby only a monometallic salt of 4,4'-DDS is precipitated and separated. The precipitate is easily purified by acid treatment into a highly purified 4,4'-DDS (by the purification method, e.g. as disclosed in Japanese Unexamined Patent Publication No.64-50855).

The present invention will be described below in greater detail with reference to the following examples.

The compositions of the products obtained in the examples were confirmed by a high performance liquid chromatography.

REFERENCE EXAMPLE 1

A 100.0 g quantity of 98.1% sulfuric acid (1.00 mole of sulfuric acid) was added dropwise with stirring to a mixture of 188.2 g (2.00 moles) of phenol and 100 ml of mesitylene. The resulting mixture was heated with stirring in an oil bath. At about 145° C., the reaction mixture began to boil to initiate the distillation. The distillate was condensed by a condenser and separated into two phases in a trap. The upper organic phase was continuously returned to the reaction system. After about 5 hours of heating, the temperature of the reaction system reached 165° C., 38 ml of water was removed therefrom to the lower phase of the trap and both values remained constant. The suspension containing DDS and phenolsulfonic acid was thus obtained. The product obtained at this stage had a composition (ratio by weight) of 4,4'-DDS:2,4'-DDS:tri-compound=93.6:4.3:2.1 The total yield of the three components was 97.0% and the yield of 4,4'-DDS alone was 90.7%, based on the sulfuric acid used.

REFERENCE EXAMPLE 2

A 100.0 g quantity of 98.1% sulfuric acid (1.00 mole of sulfuric acid) was added dropwise with stirring to a mixture of 190.1 g (2.02 moles) of phenol and 190 ml of mesitylene. The resulting mixture was heated with stirring in an oil bath. At about 145° C., the reaction mixture began to boil to initiate the distillation. The distillate was condensed by a condenser and separated into two phases in a trap. The upper organic phase was continuously returned to the reaction system. After about 5 hours of heating, the temperature of the reaction system reached 165° C., 38 ml of water was removed therefrom to the lower phase of the trap and both values remained constant. The suspension containing DDS and phenolsulfonic acid was thus obtained. The product obtained at this stage had a composition (ratio by weight) of 4,4'-DDS:2,4'-DDS:tri-compound=89.4:8.3:2.3. The total yield of the three components was 95.7% and the yield of 4,4'-DDS alone was 85.6%, based on the sulfuric acid used.

REFERENCE EXAMPLE 3

A 100.0 g quantity of 98.1% sulfuric acid (1.00 mole of sulfuric acid) was added dropwise with stirring to a mixture of 190.1 g (2.02 moles) of phenol and 190 ml of mesitylene. The resulting mixture was heated with stirring in an oil bath. At about 145° C., the reaction mixture began to boil to initiate the distillation. The distillate was condensed by a condenser and separated into two phases in a trap. The upper organic phase was continuously returned to the reaction system. After about 4 hours of distillation, (After about 5 hours of heating), the temperature of the reaction system reached 165° C., 38 ml of water Was removed therefrom to the lower phase of the trap and both values remained constant. The reaction was further continued in this state for two hours with substantially no change in the temperature of the reaction system and in the amount of water removed. In this way, the suspension containing DDS and phenolsulfonic acid was thus obtained. The product obtained at this stage had a composition (ratio by weight) of 4,4'-DDS:2,4'-DDS:tri-compound=91.7:6.0:2.3. The total yield of the three components was 97.0% and the yield of 4,4'-DDS alone was 88.9%, based on the sulfuric acid used.

REFERENCE EXAMPLE 4

The dehydration reaction was conducted in the same manner as in Reference Example 3 except that the amount of phenol used was 2.10 moles, whereby a suspension was obtained. The product obtained at this stage had a composition (ratio by weight) of 4,4'-DDS:2,4'-DDS:tri-compound=88.4:10.2:1.4. The total yield of the three components was 95.7% and the yield of 4,4'-DDS was 84.6%, based on the sulfuric acid used.

REFERENCE EXAMPLE 5

The dehydration reaction was conducted in the same manner as in Reference Example 3 except that the amount of phenol used was 2.20 moles, whereby a suspension was obtained. The product obtained at this stage had a composition (ratio by weight) of 4,4'-DDS:2,4'-DDS:tri-compound=86.5:12.5:1.0. The total yield of the three components was 93.6% and the yield of 4,4'-DDS was 81.0%, based on the sulfuric acid used.

REFERENCE EXAMPLE 6

A 100.0 g quantity of 98.0% sulfuric acid (1.00 mole of sulfuric acid) was added dropwise with stirring to a mixture of 195.7 g (2.08 moles) of phenol and 190 ml of orthodichlorobenzene, and the resulting mixture was heated. The reaction mixture began to boil at about 150° C. to initiate the distillation. The distillate was condensed by a condenser and separated into two phases in a trap. The lower organic phase was continuously returned to the reactor. After about 5 hours of heating, the temperature of the reaction system reached 179° C., and the production of water stopped. When the amount of water removed and placed in the trap reached 37 ml and both values remained constant, 150 ml of orthodichlorobenzene was added to the reaction mixture. Thereafter the reaction mixture was cooled to give a slurry. The slurry of reaction mixture was filtered at 50° C. for separation into solids and liquids, whereby a crystal powder mixture having the phenolsulfonic acid adsorbed thereon was produced.

The obtained crystal powder mixture had a composition (ratio by weight) of 4,4'-DDS:2,4'-DDS:tri-compound=80.3:17.7:2.0. The total yield of the three components was 82.1% and the yield of 4,4'-DDS was 65.9%, based on the sulfuric acid used.

REFERENCE EXAMPLE 7

A 100.0 g quantity of 98.0% sulfuric acid (1.00 mole of sulfuric acid) was added dropwise with stirring to a mixture of 202.3 g (2.15 moles) of phenol and 190 ml of orthodichlorobenzene, and the resulting mixture was heated. The reaction mixture began to boil at about 150° C. to initiate the distillation. The distillate was condensed by a condenser and separated into two phases in a trap. The lower organic phase was continuously returned to the reactor. After about 5 hours of heating, the temperature of the reaction system reached 179° C., and the production of water stopped. The amount of water removed and placed into the trap reached 37 ml and both values remained constant. The reaction was further continued in this state for two hours with substantially no change in the temperature of the reaction system and in the amount of water removed. The product obtained at this stage had a composition (ratio by weight) of 4,4'-DDS:2,4'-DDS:tri-compound=76.0:20.1:3.9. The total yield of the three components was 92.0% and the yield of 4,4'-DDS alone was 69.9%, based on the sulfuric acid used.

Substantially all of the liquid portion was gradually collected from the obtained product over a period of 1 hour in an oil bath of 110° C. and the reduced pressure in the reaction system was controlled, thereby producing a crystal powder of no consistency (free flowing). The crystal powder thus obtained had a composition (ratio by weight) of 4,4'-DDS:2,4'-DDS:tri-compound=76.2:19.9:3.9. The total yield of the three components was 92.2% and the yield of 4,4'-DDS was 70.3%, based on the sulfuric acid used.

EXAMPLE 1

The suspension obtained in Reference Example 1 was heated in an oil bath at 165° C. and the reduced pressure in the reaction system was controlled, whereby substantially all of the liquid portion was gradually collected over a period of 3 hours to complete isomerization reaction.

The product thus obtained had a composition (ratio by weight) of 4,4'-DDS:2,4'-DDS:tri-compound=96.9:1.6:1.5. The total yield of the three components calculated relative to the starting materials used was 98.5% and the yield of 4,4'-DDS was 95.4%, based on the sulfuric acid used.

EXAMPLE 2

The isomerization reaction was conducted in the same manner as in Example 1, using the suspension obtained in Reference Example 3.

The product thus obtained had a composition (ratio by weight) of 4,4'-DDS:2,4'-DDS:tri-compound=96.2:1.8 2.0. The total yield of the three components calculated relative to the starting materials used was 98.1% and the yield of 4,4'-DDS was 94.4%, based on the sulfuric acid used.

EXAMPLE 3

The isomerization reaction was conducted in the same manner as in Example 1, using the suspension obtained in Reference Example 4.

The product thus obtained had a composition (ratio by weight) of 4,4'-DDS:2,4'-DDS:tri-compound=96.1:2.0:1.9. The total yield of the three components calculated relative to the starting materials used was 96.3% and the yield of 4,4'-DDS was 92.5%, based on the sulfuric acid used.

EXAMPLE 4

The isomerization reaction was conducted in the same manner as in Example 1, using the suspension obtained in Reference Example 5.

The product thus obtained had a composition (ratio by weight) of 4,4'-DDS:2,4'-DDS:tri-compound=96.0:2.3:1.7. The total yield of the three components calculated relative to the starting materials used was 95.5% and the yield of 4,4'-DDS was 91.7%, based on the sulfuric acid used.

EXAMPLE 5

The suspension obtained in Reference Example 3 was heated in an oil bath of 180° C. and the reduced pressure in the reaction system was controlled, whereby substantially all of the liquid portion was gradually collected over a period of 3 hours, whereupon the isomerization reaction was completed. The product thus obtained had a composition (ratio by weight) of 4,4'-DDS:2,4'-DDS:tri-compound=4.7:2.5:2.8. The total yield of the three components calculated relative to the starting materials used was 97.5% and the yield of 4,4'-DDS was 92.3%, based on the sulfuric acid used.

EXAMPLE 6

The suspension obtained in Reference Example 2 was heated in an oil bath of 165° C. and the reduced pressure in the reaction system was controlled, whereby substantially all of the liquid portion was collected over a period of 30 minutes. Thereafter the pressure was restored to normal pressure by introduction of nitrogen. The product obtained at this stage had a composition (ratio by weight) of 4,4'-DDS:2,4'-DDS:tri-compound=91.1:6.7:2.2. The total yield of the three components calculated relative to the starting materials used was 97.5% and the yield of 4,4'-DDS was 88.8%, based on the sulfuric acid used.

The obtained crystal powder was further heated in an oil bath of 165° C. for three hours to complete isomerization reaction. The product thus obtained had a composition (ratio by weight) of 4,4'-DDS:2,4'-DDS:tri-compound=97.2:1.5:1.3. The total yield of the three components calculated relative to the starting materials used was 98.7% and the yield of 4,4'-DDS was 95.9%, based on the sulfuric acid used.

EXAMPLE 7

The isomerization was completed in the same manner as in Example 6, using the suspension obtained in Reference Example 4. The crystal powder obtained on completion of collection of substantially all of the liquid portion had a composition (ratio by weight) of 4,4'-DDS:2,4'-DDS:tri-compound=88.9:9.7:1.4. The total yield of the three components calculated relative to the starting materials used was 95.9% and the yield of 4,4'-DDS was 85.3%, based on the sulfuric acid used.

The product had a composition (ratio by weight) of 4,4'-DDS:2,4'-DDS:tri-compound=96.7:1.9:1.4. The total yield of the three components calculated relative to the starting materials used was 96.5% and the yield of 4,4'-DDS was 93.3%, based on the sulfuric acid used.

EXAMPLE 8

The isomerization was completed in the same manner as in Example 6, using the suspension obtained in Reference Example 5. The product obtained upon completion of collection of substantially all of the liquid portion had a composition (ratio by weight) of 4,4'-DDS:2,4'-DDS:tri-compound=88.8:9.9:1.3. The total yield of the three components calculated relative to the starting materials used was 95.1% and the yield of 4,4'-DDS was 84.4%, based on the sulfuric acid used.

The product thus obtained had a composition (ratio by weight) of 4,4'-DDS:2,4'-DDS:tri-compound=96.6:2.1:1.3. The total yield of the three components calculated relative to the starting materials used was 95.9% and the yield of 4,4'-DDS was 92.6%, based on the sulfuric acid used.

EXAMPLE 9

The suspension obtained in Reference Example 3 was heated in an oil bath of 180° C. and the reduced pressure in the reaction system was controlled, whereby substantially all of the liquid portion was gradually collected over a period of 30 minutes. Thereafter the pressure was restored to normal pressure by introduction of nitrogen. The product obtained at this stage had a composition (ratio by weight) of 4,4'-DDS:2,4'-DDS tri-compound=92.1:5.6:2.3. The total yield of the three components calculated relative to the starting materials used was 97.2% and the yield of 4,4'-DDS was 89.5%, based on the sulfuric acid used.

The obtained crystal powder was further heated in an oil bath of 165° C. for three hours to complete the isomerization reaction.

The product thus obtained had a composition (ratio by weight) of 4,4'-DDS:2,4'-DDS:tri-compound=95.5:2.3:2.2. The total yield of the three components calculated relative to the starting materials used was 98.0% and the yield of 4,4'-DDS was 93.6%, based on the sulfuric acid used.

EXAMPLE 10

The suspension obtained in Reference Example 1 was cooled to 100° C. and filtered for separation into solids and liquids. The product obtained at this stage had a composition (ratio by weight) of 4,4'-DDS:2,4'-DDS:tri-compound=93.9:4.1:2.0. The total yield of the three components calculated relative to the starting materials used was 96.8% and the yield of 4,4'-DDS was 90.9%, based on the sulfuric acid used. The obtained crystal powder was fed to the reactor in an oil bath maintained at 165° C. and the mesitylene and the like adsorbed were distilled off under reduced pressure for 15 minutes. The residue was further heated in a hermetically sealed reactor under reduced pressure with stirring at the same temperature for 3 hours to complete the isomerization.

The product thus obtained had a composition (ratio by weight) of 4,4'-DDS:2,4'-DDS:tri-compound=97.0:1.6:1.4. The total yield of the three components calculated relative to the starting materials used was 98.2% and the yield of 4,4'-DDS was 95.3%, based on the sulfuric acid used.

EXAMPLE 11

The suspension obtained in Reference Example 3 was cooled to 160° C. and filtered for separation into solids and liquids. The product obtained at this stage had a composition (ratio by weight) of 4,4'-DDS:2,4'-DDS:tri-compound=92.9:4.8:2.3. The total yield of the three components calculated relative to the starting materials used was 95.7% and the yield of 4,4'-DDS was 88.9%, based on the sulfuric acid used. The isomerization was completed in the same manner as in Example 10.

The product thus obtained had a composition (ratio by weight) of 4,4'-DDS:2,4'-DDS:tri-compound=96.5:1.8:1.7. The total yield of the three components calculated relative to the starting materials used was 96.0% and the yield of 4,4'-DDS was 92.6%, based on the sulfuric acid used.

EXAMPLE 12

The crystal powder mixture obtained in Reference Example 6 was fed to the reactor in an oil bath maintained at 165° C., and the solvent and the like adsorbed on the crystals were distilled off under reduced pressure for 30 minutes. The residue was further heated in an oil bath of 165° C. in the atmosphere of nitrogen at normal pressure with stirring for 6 hours to complete the isomerization. The product thus obtained had a composition (ratio by weight) of 4,4'-DDS:2,4'-DDS:tri-compound=96.2:2.1:1.7. The total yield of the three components calculated relative to the starting materials used was 83.0% and the yield of 4,4'-DDS was 79.8%, based on the sulfuric acid used.

EXAMPLE 13

The crystal powder obtained in Reference Example 7 was further heated at 165° C. for three hours to complete the isomerization reaction. The crystal powder thus obtained had a composition (ratio by weight) of 4,4'-DDS:2,4'-DDS:tri-compound=94.5:3.7:1.8. The total yield of the three components calculated relative to the starting materials used was 93.0% and the yield of 4,4'-DDS was 87.9%, based on the sulfuric acid used.

EXAMPLE 14

A commercial DDS was analyzed and was found to have a composition (ratio by weight) of 4,4'-DDS:2,4'-DDS:tri-compound=83.1:15.1:1.8. A 100 ml quantity of mesitylene and 3.0 g of benzenesulfonic acid were added to 100 g of this crystal powder, and the mixture was suspended. The suspension thus obtained was heated in an oil bath of 165° C. and the reduced pressure in the reaction system was controlled, whereby substantially all of the of mesitylene was collected over a period of 30 minutes. Benzenesulfonic acid was added to and evenly adsorbed on DDS. Thereafter the pressure was restored to normal pressure by introduction of nitrogen. The product obtained at this stage had a composition (ratio by weight) of 4,4'-DDS:2,4'-DDS:tri-compound=84.4:13.8:1.8.

The obtained crystal powder was further heated with stirring in an oil bath of 165° C. for three hours to complete isomerization reaction. The product thus obtained had a composition (ratio by weight) of 4,4'-DDS:2,4'-DDS:tri-compound=95.9:2.4:1.7.

EXAMPLE 15

The same suspension as used in Example 14 was heated in an oil bath of 165° C. and the reduced pressure in the reaction system was controlled so as to gradually collect substantially all of the liquid portion over a period of 3 hours. The product thus obtained had a composition (ratio by weight) of 4,4'-DDS:2,4'-DDS:tri-compound=95.8:2.5:1.7.

We claim:

1. A process for preparing 4,4'-dihydroxydiphenylsulfone, comprising heating a mixture of 4,4'-dihydroxydiphenylsulfone and 2,4'-dihydroxydiphenylsulfone in the presence of an acid catalyst to isomerize the 2,4'-dihydroxydiphenylsulfone into 4,4'-dihydroxydiphenylsulfone, wherein is selected one of (a) a suspension of 4,4'-dihydroxydiphenylsulfone and 2,4'-dihydroxydiphenylsulfone in a liquid dispersing medium is heated for isomerization while a liquid portion is distilled off, the entire liquid portion being distilled off upon or before completion of the isomerization reaction and (b) a crystal mixture of 4,4'-dihydroxydiphenylsulfone and 2,4'-dihydroxydiphenylsulfone is heated for isomerization to produce 4,4'-dihydroxydiphenylsulfone in the form of crystal powder.

2. A process according to claim 1 wherein the isomerization is conducted by heating the suspension of 4,4'-dihydroxydiphenylsulfone and 2,4'-dihydroxydiphenylsulfone in a liquid dispersing medium.

3. A process according to claim 2 wherein the distillation of substantially all of the liquid portion is completed substantially simultaneously with the completion of the isomerization reaction.

4. A process according to claim 2 wherein substantially all of the liquid portion is distilled off before completion of the isomerization reaction, and thereafter the solid phase containing 4,4'-dihydroxydiphenylsulfone and 2,4'-dihydroxydiphenylsulfone is further heated to complete the isomerization reaction.

5. A process according to claim 2 wherein the liquid dispersing medium is mesitylene.

6. A process according to claim 1 wherein the isomerization is conducted by heating a crystal powder mixture of 2,4'-dihydroxydiphenylsulfone and 4,4'-dihydroxydiphenylsulfone.

7. A process according to any one of claims 1 to 6 wherein the mixture is heated to 120° to 200° C.

* * * * *